US005618522A

United States Patent [19]
Kaleta et al.

[11] Patent Number: 5,618,522
[45] Date of Patent: Apr. 8, 1997

[54] EMULSION COMPOSITIONS

[75] Inventors: James E. Kaleta, Landen; Paul R. Tanner, Maineville; George E. Deckner, Cincinnati; Carlos G. Linares, Loveland; Steve G. Fishter, Harrison, all of Ohio

[73] Assignee: The Procter & Gamble Company, Cincinnati, Ohio

[21] Appl. No.: 376,324

[22] Filed: Jan. 20, 1995

[51] Int. Cl.$^6$ ............................. A61K 7/44; A61K 7/40
[52] U.S. Cl. ............................. 424/60; 514/63; 514/159; 514/557; 514/844
[58] Field of Search .................. 424/59, 60; 514/63, 514/844, 159, 557

[56] References Cited

U.S. PATENT DOCUMENTS

| | | | |
|---|---|---|---|
| 4,536,399 | 8/1985 | Flynn | 514/63 |
| 4,798,679 | 1/1989 | Castro et al. | 252/174.15 |
| 4,804,532 | 2/1989 | Busch, Jr. | 424/69 |
| 4,822,600 | 4/1989 | Wortzman | 424/59 |
| 4,837,011 | 6/1989 | Macchio et al. | 424/69 |
| 4,906,459 | 3/1990 | Cobb et al. | 424/70 |
| 5,082,660 | 1/1992 | Ounanian et al. | 424/63 |
| 5,223,559 | 6/1993 | Arraudeau et al. | 524/47 |
| 5,250,652 | 10/1993 | Langer | 528/125 |
| 5,288,481 | 2/1994 | Ounanian et al. | 424/63 |
| 5,320,834 | 6/1994 | Ounanian et al. | 424/63 |

FOREIGN PATENT DOCUMENTS

| | | |
|---|---|---|
| 400546 | 12/1990 | European Pat. Off. . |
| 248600 | 8/1987 | German Dem. Rep. . |
| 248599 | 8/1987 | German Dem. Rep. . |
| 51129884 | 11/1976 | Japan . |
| 62067015 | 3/1987 | Japan . |
| 62100554 | 5/1987 | Japan . |
| 02019310 | 1/1990 | Japan . |
| 03261707 | 11/1991 | Japan . |
| 04128209 | 4/1992 | Japan . |
| 9102515 | 4/1991 | Rep. of Korea . |

OTHER PUBLICATIONS

"Blurring of Wrinkles Through Control of Optical Properties," Nakamura et al., *Preprints of XIVth I.F.S.C.C. Congress*, vol. 1, Sep. 1986.

Technical Data Sheet, Cabot Corporation, "CAB–O–Sil® TS–530, Treated Fumed Silica," Copyright 1991, dated Dec. 1992.

Technical Data Sheet, Cabot Corporation, "CAB–O–Sil® TS–610, Treated Fumed Silica," Copyright 1991, dated Dec. 1992.

Technical Data Sheet, Cabot Corporation, "CAB–O–Sil® TS–720, Treated Fumed Silica," Copyright 1991, dated Dec. 1992.

Technical Data Sheet, Cabot Corporation, "CAB–O–Sil® Fumed Silica, in Cosmetic and Personal Care Products," Copyright 1992, dated Mar. 1992.

Technical Data Sheet, Dow Corning Corporation, Polymeric Transport™ "Personal Care Systems, Polytrap® 6603 Polymer Powder," Copyright 1992.

*Primary Examiner*—C. Warren Ivy
*Assistant Examiner*—Evelyn Huang
*Attorney, Agent, or Firm*—Anthony D. Sabatelli; David K. Dabbiere

[57] ABSTRACT

The present invention relates to oil-in-water emulsion compositions useful for topical application to human skin. These compositions comprise from about 5% to about 60% by weight of the total composition of an oil phase having a viscosity from about 3000 cps to about 10,000,000 cps, wherein the oil phase comprises from about 0.1% to about 10% by weight of the total composition of a particulate thickener for the oil phase, and from 0% to about 10% by weight of the total composition of an oil phase emulsifier. These compositions also comprise from about 40% to about 95% by weight of the total composition of an aqueous phase selected from the group consisting of water, water-miscible solvents, and mixtures thereof, wherein the aqueous phase comprises from 0% to about 10% by weight of the total composition of an aqueous phase emulsifier. In these compositions the weight percentages of the oil phase emulsifier and of the aqueous phase emulsifer are not simultaneously zero.

17 Claims, No Drawings ns**

EMULSION COMPOSITIONS

TECHNICAL FIELD

The present invention relates to oil-in-water emulsion compositions useful for topical application to human skin. These compositions have an aesthetically pleasing skin feel and are also useful for delivering a wide variety of active ingredients to the skin.

BACKGROUND OF THE INVENTION

The treatment of the skin with topical compositions has been known is since the dawn of civilization. Today, a wide variety of skin treatment compositions are available to the consumer including moisturizers, anti-acne compositions, sunscreens, make-ups, topical anesthetics, artificial tanning compositions, skin lightening compositions, anti-wrinkle compositions, and the like.

As the number of skin treatment products grows, so does the need for providing products which deliver improved benefits to consumers. For example, it is desirable to provide products which are easy to apply and which form a smooth, uniform film upon the skin surface. It is desirable to provide products which are not greasy or sticky and which have an aesthetically appealing skin feel. It is desirable to provide products which can be used to deliver active ingredients to the skin and which are substantive such that the active ingredient is not easily lost from the skin by rub-off, wash-off, perspiration, or overly-rapid penetration through the skin.

Examples of topical products that are particularly difficult to formulate are those containing an active ingredient that is potentially irritating to the skin, and those that utilize a costly active ingredient. In the case of products in which the active ingredient is potentially irritating to the skin, it is desirable to obtain the benefit from the active while minimizing the potential skin irritation effects. In the case of products in which the active is costly, it is desirable to maximize the benefit from the active while minimizing the amount of active to be formulated. For example, with sunscreen products, it is a challenge for formulators to maximize the sun protection from the sunscreen active or actives while minimizing the potentially irritating effects of the active and also keeping down formulation costs by utilizing the lowest level of sunscreen possible.

It is, therefore, seen from the above discussion that topical skin care compositions can be improved in a variety of ways.

One approach to improving topical skin care products is by the addition of film-forming polymers and thickeners. However, most film-forming polymers and thickeners tend to be greasy and sticky, thereby imparting undesirable aesthetic qualities to the product. Many of these materials also have less than ideal rheological properties and yield products that are stringy, lumpy, and difficult to apply to the skin. Many of these materials can only be used over a narrow formulation pH range. Also, many of these materials are incompatible with various active ingredients.

It is found in the present invention that highly useful oil-in-water emulsion compositions can be prepared by utilizing the particulate thickener materials described herein to thicken the oil phase of the emulsion. These particulate thickeners overcome many of the disadvantages of conventional film-forming polymers and thickeners. These particulate thickeners are known for use in industrial products such as coatings, adhesives, and sealants, but have seen relatively little use in the personal care products area.

The emulsions of the present invention also utilize at least one oil phase emulsifier or at least one aqueous phase emulsifier.

The oil phase of these emulsions is thickened to achieve a relatively high viscosity, i.e., from about 3000 cps, measured at 25° C. using a Brookfied RVT viscometer equipped with a T bar "B" spindle rotating at 5 rpm, to about 10,000,000 cps, measured at 25° C. using a Brookfied RVT viscometer equipped with a T bar "F" spindle rotating at 0.5 rpm, which, surprisingly, yields emulsions with highly desirable characteristics. It is found that these emulsions are nongreasy and nonsticky and have a smooth feel. These emulsions are easy to apply and spread upon the skin and form a smooth, uniform film upon the skin surface. These emulsions can be formulated over a wide pH range and are compatible with a large variety of active ingredients. These emulsions are also useful for delivering sunscreen actives and other actives which are potentially irritating to the skin.

It is, therefore, an object of the present invention to provide oil-in-water emulsion compositions that are useful for topical application to human skin.

It is another object to provide emulsions which are not sticky or greasy and which are aesthetically pleasing to the user.

It is another object of the present invention to provide emulsions which can be formulated over a wide range of pH values and which are compatible with a wide range of active ingredients.

It is another object of the present invention to provide emulsions which are highly substantive and which also provide substantivity for any active ingredients.

It is another object of the present invention to provide emulsions which are nonirritating to human skin and which help to mitigate the effects of potentially irritating active ingredients.

It is another object of the present invention to provide emulsions in which mitigate the penetration of potentially irritating actives through the skin.

It is another object of the present invention to provide emulsions which also comprise at least one sunscreen active and which are useful for providing protection against the harmful effects of ultraviolet radiation.

It is another object of the present invention to provide methods of treatment of human skin with the oil-in-water emulsions described herein.

These and other objects will become readily apparent from the detailed description which follows.

SUMMARY OF THE INVENTION

The present invention relates to an oil-in-water emulsion composition useful for topical application to human skin comprising:
  (a) from about 5% to about 60% by weight of the total composition of an oil phase having a viscosity from about 3000 cps, measured at 25° C. using a Brookfied RVT viscometer equipped with a T bar "B" spindle rotating at 5 rpm, to about 10,000,000 cps, measured at 25° C. using a Brookfied RVT viscometer equipped with a T bar "F" spindle rotating at 0.5 rpm, wherein said oil phase comprises
    (i) from about 0.1% to about 10% by weight of the total composition of a particulate thickener selected from the group consisting of silica, treated silica, polymethacrylate polymers, polymethacrylate and styrene copolymers, calicum silicate, treated calcium silicate, treated bentonite, treated hectorite, and mixtures thereof; and (ii) from 0% to about 10% by weight of the total composition of an oil phase emulsifier; and (b) from about 40% to about 95% by weight of the total composition of an aqueous phase selected from the group consisting of water, water-miscible solvents, and mixtures thereof, wherein said aqueous phase comprises (i) from 0% to about 10% by weight of the total composition of an aqueous phase emulsifier, wherein the percentage by weight of the oil phase emulsifier and of the aqueous phase emulsifier are not simultaneously zero.

All percentages and ratios used herein, unless otherwise indicated, are by weight and all measurements made are at 25° C., unless otherwise designated. The invention hereof can comprise, consist of, or consist essentially of, the essential as well as optional ingredients and components described herein.

DETAILED DESCRIPTION OF THE INVENTION

The term "useful for topical application to human skin," as used herein, means that the oil-in-water emulsions of the present invention are suitable for application to the human skin surface without undue toxicity or other untoward effects, and can be used to deliver a wide variety of optional ingredients to the skin.

The compositions of the present invention are in the form of oil-in-water emulsions. In other words, these compositions are formulated to have a discontinuous oil phase that is dispersed in a water, i.e., aqueous, phase. In these emulsions the oil phase is thickened as described herein to meet the requisite viscosity requirements. In contrast, conventional oil-in-water emulsions typically have an oil phase with a relatively low viscosity. Without being limited by theory, it is believed that this high viscosity oil phase provides compositions having the highly desirable properties described herein.

OIL PHASE

The oil-in-water emulsion compositions comprise from about 5% to about 60% by weight of the total composition, preferably from about 7% to about 40% by weight of the total composition, and more preferably from about 10% to about 25% by weight of the total composition of an oil phase.

The oil phase also comprises a particulate thickener and an oil phase emulsifier, as described herein.

The oil phase has a viscosity from about 3000 cps to about 10,000,000 cps, preferably from about 5000 cps to about 1,000,000 cps, and more preferably from about 20,000 cps to about 80,000 cps. The viscosity of the oil phase is measured using standard techniques familiar to one of ordinary skill in the art. A preferred method for measuring the viscosity of the oil phase is with a Brookfield RVT viscometer, available from Brookfield Engineering Laboratories, Stoughton, MA. In the present invention, viscosity values up to and including 80,000 cps, are determined using a Brookfied RVT viscometer equipped with a T bar "B" spindle rotating at 5 rpm, and viscosity values over 80,000 cps are determined using a Brookfied RVT viscometer equipped with a T bar "F" spindle rotating at 0.5 rpm. It is also preferable, but not essential, that the thickened oil phase be thixotropic. The term thixotropic is familiar to one of ordinary skill in the art and refers to a substance whose viscosity decreases when subjected to shear. It is also preferable, but not essential, that the thixotropic behavior of the oil phase is reversible such that when shear is discontinued, the oil phase returns to or approaches its original viscosity.

The oil phase of the present invention comprises one or more oils or oil phase components commonly known to one of ordinary skill in the art in the preparation of oil-in-water emulsions. These oils or oil phase components materials generally having low solubility in water, i.e., less than about 10%, preferably less than about 5%, and more preferably less than about 1%, by weight in water at 25° C.

Preferably, the oil phase, excluding the particulate thickener, has a weighted arithmetic mean solubility parameter below 11. Solubility parameters are well known to the formulation chemist of ordinary skill in the art and are routinely used as a guide for determining the compatibility and solubility of materials in the formulation process.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$=the sum of the heat of vaporization additive group contributions, and $\sum_i m_i$=the sum of the molar volume additive group contributions Standard tabulations of heats of vaporization and molar volume additive group contributions for a wide variety of atoms and groups of atoms are collected in Barton, A.F.M., *Handbook of Solubility Parameters*, CRC Press, Chapter 6, Table 3, pp. 64–66 (1985), which is incorporated by reference herein in its entirety. The above solubility parameter equation is described in Fedors, R.F., "A Method for Estimating Both the Solubility Parameters and Molar Volumes of Liquids," Polymer Engineering and Science, vol. 14, no. 2, pp. 147–154 (February 1974), which is incorporated by reference herein in its entirety.

Solubility parameters obey the law of mixtures such that the solubility parameter for a mixture of materials is given by the weighted is arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heats of vaporization in the *Handbook of Solubility Parameters* are reported in units of kJ/mol. However, these tabulated heat of vaporization values are readily converted to cal/mol using the following well-known relationships:

1J/mol=0.239006 cal/mol and 1000 J=1 kJ.

See, Gordon, A.J., et al., *The Chemist's Companion*, John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters*.

Nonlimiting examples of suitable oils and oil phase components include hydrocarbons, silicones, fatty alcohols, fatty acids, esters (including monoglycerides, diglycerides, and triglycerides), ethers, and the like. Oils and oil phase components useful in the instant invention are further described in U.S. Pat. No. 4,919,934, to Deckner et al., issued Apr. 24, 1990, which is incorporated herein by reference in its entirety.

Volatile silicone components such as cyclic polydimethylsiloxanes containing from about 3 to about 9 silicon atoms, and dimethicone are useful herein. Nonvolatile silicones include polyalkylsiloxanes and polyalkylaryl siloxanes. Useful volatile and nonvolatile silicones are disclosed in U.S. Pat. No. 5,069,897, to Orr, issued Dec. 3, 1991, which is incorporated by reference herein in its entirety.

PARTICULATE THICKENER

The oil phase of the present invention comprises a particulate thickener. The particulate thickener comprises from about 0.1% to about 10% by weight of the total composition, preferably from about 0.25% to about 5% by weight of the total composition, and more preferably from about 0.5% to about 1.5% by weight of the total composition.

The term "particulate thickener" means that the thickener is in the form of small, finely divided particles having a mean diameter of less than about 100 microns. The particulate thickener is essentially insoluble in the oil phase and is dispersed therein. The particulate thickener has a solubility of less than about 10%, preferably less than about 5%, and more preferably less than about 1% by weight of the oil phase, including the oil phase emulsifier, at 25° C.

The oil phase comprises from about 0.1% to about 10% by weight of the total composition of a particulate thickener selected from the group consisting silica, treated silica, polymethacrylate polymers, polymethacrylate and styrene copolymers, calicum silicate, treated calcium silicate, treated bentonite, treated hectorite, and mixtures thereof.

A preferred particulate thickener for use herein is fumed silica. More preferred for use herein is surface-treated fumed silica. Even more preferred is a fumed silica selected from the group consisting of polyalkylsiloxane treated fumed silica, trialkylsilanized fumed silica, dialkyldisilanized fumed silica, and mixtures thereof. Most preferred is a fumed silica selected from the group consisting of polydimethylsiloxane treated fumed silica, trimethylsilanized fumed silica, dimethyldisilanized fumed silica, and mixtures thereof.

Silica and Surface-Treated Silica

Silica is also known as silicon dioxide or silicic anhydride. Silica is a material which can be represented by the chemical formula $SiO_2$. See, *The Merck Index*, tenth edition, 1983, entry 8329, page 1220, which is incorporated by reference herein in its entirety. A variety of different types of silicas which are useful herein, are known including fumed or arced silica, precipitated silica, silica gel, amorphous silica, and silica sols and colloids.

Fumed silica, which is also known as arced silica, is produced by the vapor phase hydrolysis of silicon tetrachloride in a hydrogen oxygen flame. Without being limited by theory, it is believed that the combustion process creates silicon dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. Amorphous silicas are generally naturally occurring microcrystalline forms of the material. Silica sols and colloids are dispersions of amorphous silica in an aqueous solution. See, Bergna, Horacio E., Ed., "The Colloid Chemistry of Silica," *Ralph K. Iler Memorial Symposium*, 200th National Meeting, American Chemical Society, Washington, D.C., 1994; Kirk-Othmer, *Encyclopedia of Chemical Technology*, Vol. 20, 3rd Ed., 1982; and *Cabot Technical Data Pamphlet TD-104* entitled "CAB-O-SIL® Fumed Silica in Cosmetic and Personal Care Products," March 1992, which are all incorporated by reference herein in their entirety.

The fumed silica and treated fumed silica preferably have a mean particle size for the agglomerates, i.e., a mean agglomerate particle size, of from about 0.1 microns to about 100 microns, preferably from about 1 micron to about 50 microns, and more preferably from about 10 microns to about 30 microns. The agglomerates are composed of aggregates which having a mean particle size, i.e., a mean aggregate particle size, from about 0.01 microns to about 15 microns, preferably from about 0.05 microns to about 10 microns, more preferably from about 0.1 microns to about 5 microns, and most preferably from about 0.2 microns to about 0.3 microns.

The fumed silica agglomerates typically have active hydroxyl groups. It is desirable to treat these fumed silicas to render the hydroxyl groups less reactive. A useful method of treatment is to coat the fumed silica with a nonpolar organic compound to render the active hydroxyl groups less reactive. Preferred organic compounds for treatment include polyalkylsiloxanes, with polydimethylsiloxanes being most preferred. A commercially available polydimethylsiloxane treated fumed silica useful herein is sold under the trade name CAB-O-Sil® TS-720 Treated Fumed Silica, by Cabot Corporation, Tuscola, Ill. This material has a surface area of $100\pm20$ m$^2$/g and a bulk density of 50 g/liter. See, *Cabot Corporation Technical Data Sheet Pamphlet* entitled "CAB-O-Sil® TS-720 Treated Fumed Silica," 1991, which is incorporated by reference herein in its entirety.

Another useful method of treatment is to chemically react the hydroxyl groups of the fumed silica with a silanizing agent, e.g. diemthyldichlorosiliane or hexamethyldisilizane. In these chemically treated silicas, the free hydroxyl groups of the silica are replaced with an oxygen-silicon bond of the silanizing agent. A commercially available trimethyl silanized fumed silica is sold under the trade name CAB-0-Sil® TS-530, by Cabot Corporation, Tuscola, IL. This material has a surface area of $215\pm30$ m$^2$/g and a bulk density of 50 g/liter. See, *Cabot Corporation Technical Data Sheet Pamphlet* entitled "CAB-O-Sil® TS-530 Treated Fumed Silica," December 1992, which is incorporated by reference herein in its entirety. A commercially available dimethyldisilanized fumed silica is sold under the trade name CAB-O-SIL® TS-610, by Cabot Corporation, Tuscola, Ill. This material has a surface area of $120\pm20$ m$^2$/g and a bulk density of 50 g/liter. See, *Cabot Corporation Technical Data Sheet Pamphlet* entitled "CAB-O-Sil® TS-610 Treated Fumed Silica," December 1992, which is incorporated by reference herein in its entirety Polymethacrylate Polymers and Polymethacrylate and Styrene Copolymers Also useful herein are polymethacrylate polymers and polymethacrylate and styrene copolymers. These materials are swellable polymers which are useful for absorbing liquid compositions to provide a thickening or gelling effect on the liquid. The polymethacrylate polymers are homopolymers of methacrylic acid esters, preferably the methyl or ethyl esters, which are optionally crosslinked with any of the common crosslinking agents. The polymethacrylate and styrene copolymers are copolymers of methacrylic acid esters, preferably the methyl or ethyl esters, with styrene, which are optionally crosslinked with any of the common crosslinking agents. The crosslinking agent is most typically a material containing two or more unsaturated functional groups. The crosslinking agent is reacted with the monomer units of the polymer or copolymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal.

A particularly useful crosslinked polymethacrylate polymer is sold under the tradename Polytrap®6603, available from Dow Corning Corp., Midland, Mich.

Treated Bentonites and Treated Hectorites

Bentonite is a colloidal aluminum silicate clay. See Merck Index, Tenth Edition, 1983, entry 1051, p. 149, which is incorporated by reference herein in its entirety. Hectorite is a clay containing sodium, magnesium, lithium silicon, oxygen, hydrogen, and fluorine. See Merck Index, Tenth Edition, 1983, entry 4514, p. 667, which is incorporated by reference herein in its entirety.

Useful herein are bentonites and hectorites that have been treated with various organic compounds to render the clays less polar. By "treated," as used herein means that these materials have been coated with the organic compound. Nonlimiting examples of treated bentones include stearalkonium hectorite, quaternium-18 bentonite, quaternium-18 hectorite, castor oil (and) stearalkonium hectorite (and) propylene carbonate, isopropyl myristate (and) stearalkonium hectorie (and) propylene carbonate, isododecane (and) quaternium-18 hectorite (and) propylene carbonate, lanolin oil (and) isopropyl palmitate (and) stearalkonium hectorite (and) propylene carbonate (and) propylparaben, propylene glycol dicaprylate/dicaprate (and) stearalkonium hectorite (and) propylene carbonate, mineral oil (and) quaternium-18 hectorite (and) propylene carbonate, mineral oil (and) quaternium-18 hectorite (and) SD alcohol 40, petroleum distillates (and) quaternium-18 hectorite (and) propylene carbonate, C12–15 alkyl bnezoate (and) stearalknoium hectorite (and) propylene carbonate, cyclomethicone (and) quaternium-18 hectorite (and) SD alcohol 40, cyclomethicone (and) quaternium-18 hectorite (and) propylene carbonate, and mixtures thereof.

Calcium Silicate and Treated Calcium Silicate

Also useful herein are calcium silicate and treated calcium silicate. Common forms of calcium silicate include $CaSiO_3$, $CaSiO_4$, and $CaSiO_5$. These materials are also known as calcium salts of silicic acid. See Merck Index, Tenth. Edition, 1983, entry 1680, page 234, which is incorporated by reference herein in its entirety. The calcium silicates can be treated with a wide variety of nonpolar organic compounds to render the materials more hydrophobic and less reactive.

Useful calcium silicates include the following commercially available materials: Hubersorb (Huber Corp., Harve de Grace, Md.), and Micro-Cel C, Micro-Cel E, and Micro-Cel T-38 (Celite Corp., Denver, Colo.).

OIL PHASE EMULSIFIER

The oil phase of the emulsions of the present invention comprises an oil phase emulsifier. The oil phase emulsifier comprises from 0% to about 10% by weight of the total composition, preferably from about 0.1% to about 5% of the total composition, and more preferably from about 0.25% to about 1% of the total composition.

The term "oil phase emulsifier" means an emulsifier which is processed or formulated into the oil phase of the oil-in-water emulsion. Preferably, the oil phase emulsifier has an HLB value below 12, more preferably from about 3 to below 12, most preferably from about 3 to about 11. The term "HLB" is well known to one of ordinary skill in the art and means hydrophobic lipophilic balance. See, "The HLB System, A Time-Saving Guide to Emulsifier Selection," ICI Americas Inc., August (1984) and McCutcheon's, *Detergents and Emulsifiers*, North American Edition (1987), published by Mc Publishing Co.; which list various emulsifiers useful herein. Both of these references are incorporated herein by reference in their entirety.

Preferred oil phase emulsifiers are those selected from the group consisting of steareth-2, PEG-5 soya sterol oil, PEG-10 Soya sterol oil, diethanolamine cetyl phosphate, sorbitan monostearate, diethylenglycol monostearate, glyceryl monostearate, and mixtures thereof.

More preferred are steareth-2 and PEG-10 soya sterol oil.

Most preferred is steareth-2.

AQUEOUS PHASE

The oil-in-water emulsion composition comprises from about 40% to about 95% by weight of the total composition, preferably from about 60% to about 93% by weight of the total composition, and more preferably from about 75% to about 90% by weight of the total composition of an aqueous phase. The aqueous phase is selected from the group consisting of water, water-miscible solvents, and mixtures thereof.

Preferably, the aqueous phase has a weighted arithmetic mean solubility parameter of 11 or above.

Nonlimiting examples of water-miscible solvents include those selected from the group consisting of alcohols having from about 1 to about 6 carbon atoms, polyols having from about 1 to about 10 carbon atoms, ketones having from about 3 to about 4 carbon atoms, C1–C6 esters of C1–C6 alcohols, sulfoxides, amides, carbonate esters, ethoxylated and propoxylated C1–C10 alcohols, lactones, pyrollidones, and mixtures thereof. Preferred water-miscible solvents are those selected from the group consisting of ethanol, 2-propanol, propylene glycol, buylene glycol, and mixtures thereof.

The aqueous phase of the emulsion compositions of the present invention can also comprise one or more humectant or moisturizing materials. A variety of these materials can be employed and each can be present at a level of from about 0.1% to about 20%, more preferably from about 1% to about 10% and most preferably from about 2% to about 5%. These materials include guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. An especially preferred humectant or moisturizer material for use herein is glycerol.

AQUEOUS PHASE EMULSIFIER

The aqueous phase of the emulsions of the present invention comprises an aqueous phase emulsifier. The aqueous phase emulsifier comprises from 0% to about 10% by weight of the total composition, preferably from about 0.1% to about 5% by weight of the total composition, and more preferably from about 0.25% to about 1% by weight of the total composition.

The term "aqueous phase emulsifier" means an emulsifier which is processed or formulated into the aqueous phase of the oil-in-water emulsion. Preferably, the aqueous phase emulsifier has an HLB value of 12 or above. See, "The HLB System, A Time-Saving Guide to Emulsifier Selection," ICI Americas Inc., Aug., 1984 and *Detergents and Emulsifiers*, North American Edition (1987), published by Mc Publishing Co., which both list various emulsifiers useful herein, and which have already been incorporated herein by reference in their entirety.

Preferred aqueous phase emulsifiers are those selected from the group consisting of Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 methyl glucoside sesquistearate, PEG-20 glyceryl monostearate, sucrose monostearate, sucrose polystearates (having a high proportion of sucrose monostearate), polyglyceryl 10 stearate, polyglceryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, and mixtures thereof.

More preferred is steareth-21.

In the compositions of the present invention, the weight percentage for the oil phase emulsifier and the aqueous phase emulsifier cannot both simultaneously be zero. In other words, the compositions must always comprise at least one oil phase emulsifier or at least one aqueous phase emulsifier.

Additional Components

A wide variety of additional components can be employed in the topical oil-in-water emulsion compositions herein. Non-limiting examples include the following:

ACTIVE INGREDIENT

The compositions of the present invention can also comprise a safe and effective amount of at least one active ingredient selected from the group consisting of anti-acne actives, nonsteroidal antiinflammatory actives, anti-skin wrinkling actives, anti-pruritic actives, anesthetic actives, antimicrobial actives, sunscreening actives, sunless tanning actives, skin lightening actives, and mixtures thereof.

The phrase "safe and effective amount," as used herein in reference to the active ingredient, means an amount of an active large enough to significantly or positively bring about the desired effect or to modify the condition to be treated, but low enough to avoid serious side effects at a reasonable benefit to risk ratio, within the scope of sound medical judgement. A safe and effective amount of the active ingredient will vary with the specific active, the ability of the composition to penetrate the active through the skin, the amount of composition to be applied, the particular condition being treated, the age and physical condition of the individual being treated, the severity of the condition, the duration of the treatment, the nature of concurrent therapy, and like factors.

The active ingredients used in the compositions of the present invention preferably comprise from about 0.01% to about 30% by weight of the compositions, more preferably from about 0.05% to about 15%, and most preferably from about 0.1% to about 10%. The exact amount of the active ingredient will depend upon the active chosen. As mentioned previously, mixtures of active ingredients can also be used.

Nonlimiting examples of active ingredients from the classes listed above include those which follow. It is to be understood that the active ingredients can have more than one function and that the listing of an active ingredient in any particular class is not intended as a limitation for that material. It is also to be understood that the active ingredients are not limited to those materials which conventionally are classified as drugs, but also include materials which can be classified as cosmetics. The active ingredients useful herein can provide drug benefits, cosmetic benefits, or mixtures of benefits.

Useful active ingredients in the compositions of the present invention include anti-acne actives. Anti-acne actives for use in the present invention include the keratolytics such as salicylic acid, sulfur, lactic acid, glycolic, pyruvic acid, resorcinol, and N-acetylcysteine; retinoids such as retinoic acid and its derivatives (e.g., cis and trans); antibiotics and antimicrobials such as benzoyl peroxide, octopirox, erythromycin, zinc, tetracyclin, triclosan, azelaic acid and its derivatives, phenoxy ethanol and phenoxy propanol, ethylacetate, clindamycin and meclocycline; sebostats such as flavinoids; alpha and beta hydroxy acids; and bile salts such as scymnol sulfate and its derivatives, deoxycholate, and cholate. Preferred anti-acne actives are those selected from the group consisting of salicylic acid, sulfur, resorcinol, lactic acid, zinc, erythromycin, benzoyl peroxide, and mixtures thereof. Preferred anti-acne agents include those selected from the group consisting of salicylic acid, benzoyl peroxide, sulfur, resorcinol, zinc, erythromycin, and mixtures thereof.

Useful actives in the compositions of the present invention include non-steroidal anti-inflammatory actives or drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including, but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Useful actives in the compositions of the present invention include anti-skin wrinkling actives which help to ameliorate the effects of skin aging. Nonlimiting examples of these materials include those selected from the group consisting of salicylic acid, retinoic acid, and α-hydroxy and α-keto acids having from about 2 to about 30 carbon atoms, including compounds such as glycolic acid, lactic acid, pyruvic acid, and mixtures thereof.

Useful actives in the compositions of the present invention include antipruritic actives. Antipruritic actives preferred for inclusion in the compositions of the present invention include pharmaceutically-acceptable salts of methdilizine, trimeprazine, and mixtures thereof.

Useful actives in the compositions of the present invention include anesthetic actives. Anesthetic actives preferred for inclusion in compositions of the present invention include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine, phenol, and mixtures thereof.

Useful actives in the compositions of the present invention include antimicrobial actives such as antibacterial, antifungal, antiprotozoal and antiviral drugs. Antimicrobial actives for inclusion in compositions of the present invention include pharmaceutically-acceptable salts of b-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial actives preferred for inclusion in compositions of the present invention include tetracycline hydrochloride, erythromycin estolate, erythromycin stearate (salt), amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnaftate, clotrimazole, and mixtures thereof.

Also useful herein are sunscreen actives. A wide variety of sunscreen actives are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Preferred among the additional sunscreens are those selected from the group consisting of 2-ethylhexyl p-methoxycinnamate, 2-ethylhexyl N,N-dimethyl-p-aminobenzoate, p-aminobenzoic acid, octocrylene, oxybenzone, 2-phenylbenzimidazole-5-sulfonic acid, homomenthyl salicylate, octyl salicylate, 4,4'-methoxy -t-butyldibenzoylmethane, 4-isopropyl dibenzoylmethane, 3-benzylidene camphor, 3-(4-methylbenzylidene) camphor, triethanolamine salicylate, titanium dioxide, zinc oxide, iron oxide, and mixtures thereof.

Still other useful sunscreen actives are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreen actives disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range. These sunscreen actives provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)methylaminobenzoic acid ester of 2-hydroxy-4-(2-hydroxyethoxy)benzophenone, 4-N,N-( 2-ethylhexyl)-methylaminobenzoic acid ester of 4-(2-hydroxyethoxy)dibenzoylmethane, and mixtures thereof.

Generally, the sunscreens comprise from about 0.5% to about 30% of the compositions. Exact amounts will vary depending upon the sunscreen chosen and the desired Sun Protection Factor (SPF). SPF is a commonly used measure of photoprotection of a sunscreen against erythema. See, *Federal Register*, Vol. 43, No. 166, pp. 38206–38269, Aug. 25, 1978, which is incorporated herein by reference in its entirety.

Also useful in the present invention are sunless tanning actives including dihydroxyacetone, glyceraldehyde, indoles and their derivatives, and the like.

Other useful actives include skin lightening actives. Examples of these actives include materials selected from the group consisting of hydroquinone, ascorbic acid, kojic acid, sodium metabisulfite, and mixtures thereof.

ADDITIONAL THICKENING OR GELLING AGENTS

The compositions of the present invention can also comprise from about 0.05% to about 10%, more preferably from about 0.1% to about 5%, and most preferably from about 0.25% to about 2.5% of additional thickening or gelling agents.

Nonlimiting classes of thickening or gelling agents include those selected from the group consisting of carboxylic acid polymers, crosslinked polyacrylate polymers, polyacrylamide polymers, polysaccharides, gums, vinyl ether/ maleic anhydride copolymers, crosslinked poly(N-vinylpyrrolidones), and mixtures thereof. See, U.S. Pat. No. , 4,387,107, to Klein et al., issued Jun. 7, 1983 and "Encyclopedia of Polymer and Thickeners for Cosmetics," R. Y. Lochhead and W. R. Fron, eds., *Cosmetics & Toiletries*, vol. 108, pp. 95–135 (May 1993), which list a variety of thickening or gelling agents, and which are all incorporated herein by reference in their entirety.

Carboxylic Acid Polymers These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl —CN —COOH and mixtures thereof). The second type of polymer is a crosslinked copolymer having a first monomer selected from the group consisting of an acrylic acid monomer or derivative thereof (as just described in the previous sentence), a short chain alcohol (i e. a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acryl acid portion of the ester has substituents on the two and three carbon positions independently selected from the group consisting of $C_{1-4}$ alkyl —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters $C_{1-4}$ alcohol ethacrylate esters, and mixtures thereof, with the $C_{1-4}$ alcohol acrylate esters $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are both incorporated by reference herein in their entirety. See also, *CTFA International Cosmetic Ingredient Dictionary*, fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B.F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B.F. Goodrich. In other words, examples of carboxylic acid polymer thickeners useful herein are those selected from the group consisting of carbomers, acrylates/C10–C30 alkyl acrylate crosspolymers, and mixtures thereof.

Crosslinked Polyacrylate Polymers The crosslinked polyacrylate polymers useful as thickeners or gelling agents include both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, 1 is an integer of 0 or greater, m is an integer of 0 or greater, n is an integer of 0 or greater, but where either I or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1-C_8$, preferably $C_1-C_5$, more preferably $C_1-C_3$, and most preferably $C_1-C_2$. When quaternzied, the polymers are preferably quaternized with short is chain alkyls i.e. $C_1-C_8$, preferably $C_1-C_5$, more preferably $C_1-C_3$, and most preferably $C_1-C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein I is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-11 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which 1 is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6".

Polyacrylamide Polymers Also useful herein are polyacrylamide polymers, especially non-ionic polyacrylamide polymers including substituted branched or unbranched polymers. These polymers can be formed from a variety of monomers including acrylamide and methacrylamide which are unsubstituted or subtituted with one or two alkyl groups (preferably $C_1$ to $C_5$). Preferred are acrylate amide and methacrylate amide monomers in which the amide nitrogen is unsubstituted, or substituted with one or two $C_1$ to $C_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Polysaccharides A wide variety of polysaccharides are useful herein. By "polysaccharides" are meant gelling agents containing a backbone of repeating sugar (i.e. carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroyxalkylated (preferably hydroxyethylated or hydroxypropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1->3) linked glucose units with a (1->6) linked glucose every three units, a commercially available example of which is Clearogel™CS11 from Michel Mercier Products Inc. (Mountainside, N.J.).

Gums Other additional thickening and gelling agents useful herein include materials which are primarily derived from natural sources. Nonlimiting examples of these gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

Crosslinked Vinyl Ether/Maleic Anhydride Copolymers
Other additional thickening and gelling agents useful herein include crosslinked copolymers of alkyl vinyl ethers and maleic anhdride. In these copolymers the vinyl ethers are represented by the formula R—O—CH═CH$_2$ wherein R is a C1–C6 alkyl group, preferably R is methyl. Preferred crosslinking agents are C4–C20 dienes, preferably C6 to C16 dienes, and most preferably C8 to C12 dienes. A particularly preferred copolymer is one formed from methyl vinyl ether and maleic anhydride wherein the copolymer has been crosslinked with decadiene, and wherein the polymer when diluted as a 0.5% aqueous solution at pH 7 at 25° C. has a viscosity of 50,000–70,000 cps when measured using a Brookfield RTV viscometer, spindle #7 at 10 rpm. This copolymer has the CTFA designation PVM/MA decadiene crosspolymer and is commercially available as Stabileze$^{tm}$ 06 from International Specialty Products (Wayne N.J.).

Crosslinked poly(N-vinylpyrrolidones) Crosslinked polyvinyl(N-pyrrolidones) useful herein as additional thickening and gelling agents and include those described in U.S. Pat. No. 5,139,770, to Shih et al, issued Aug. 18, 1992, and U.S. Pat. No. 5,073,614, to Shih et al., issued Dec. 17, 1991, both patents of which are incorporated by reference herein in their entirety. These gelling agents typically contain from about 0.25% to about 1% by weight of a crosslinking agent selected from the group consisting of divinyl ethers and diallyl ethers of terminal diols containing from about 2 to about 12 carbon atoms, divinyl ethers and diallyl ethers of polyethylene glycols containing from about 2 to about 600 units, dienes having from about 6 to about 20 carbon atoms, divinyl benzene, vinyl and allyl ethers of pentaerythritol, and the like. Typically, these gelling agents have a viscosity from about 25,000 cps to about 40,000 cps when measured as a 5% aqueous solution at 25° C. using a Brookfield RVT viscometer with Spindle #6 at 10 rpm. Commercially available examples of these polymers include ACP-1120, ACP-1179, and ACP-1180, available from International Specialty Products (Wayne, N.J.).

Also useful herein are polyacrylamide polymers, especially non-ionic polyacrylamide polymers including substituted branched or unbranched polymers. These polymers can be formed from a variety of monomers including acrylamide and methacrylamide which are unsubstituted or subtituted with one or two alkyl groups (preferably C$_1$ to C$_5$). Preferred are acrylate amide and methacrylate amide monomers in which the amide nitrogen is unsubstituted, or substituted with one or two C$_1$ to C$_5$ alkyl groups (preferably methyl, ethyl, or propyl), for example, acrylamide, methacrylamide, N-methacrylamide, N-methylmethacrylamide, N,N-dimethylmethacrylamide, N-isopropylacrylamide, N-isopropylmethacrylamide, and dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Other Additional Components

The compositions of the present invention can also comprise a wide range of other additional components. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin protectants, solvents, suspending agents (nonsurfactant), ultraviolet light absorbers, and viscosity increasing agents (aqueous and nonaqueous). Examples of other functional classes of materials useful herein that are well known to one of ordinary skill in the art include emulsifiers, solubilizing agents, and sequestrants, and the like.

Nonlimiting examples of these additional components cited in the *CTFA Cosmetic Ingredient Handbook*, as well as other materials useful herein, include the following: vitamins and derivatives thereof [e.g., vitamin C, tocopherol, tocopherol acetate, and the like]; anti-oxidants; polyethyleneglycols and polypropyleneglyocls; preservatives for maintaining the antimicrobial integrity of the compositions; antioxidants; chelators and sequestrants; and aesthetic components such as fragrances, pigments, colorings, essential oils, skin senates, astringents, skin soothing agents, skin healing agents and the like, nonlimiting examples of these aesthetic components include clove oil, menthol, camphor, eucalyptus oil, eugenol, menthyl lactate, witch hazel distillate, bisabolol, dipotassium glycyrrhizinate and the like.

METHODS OF TREATING THE SKIN

The topical compositions of the present invention are used in conventional ways to treat the skin of humans. Such methods of use depend upon the type of composition employed but generally involve application of an effective amount of the product to the skin. By "effective amount" is meant an amount sufficient to provide the benefit desired. Typical amounts of the compositions of the present invention which are applied to the skin will vary depending upon the type of composition and the benefit desired, however, typical ranges are generally from about 0.1 mg/cm$^2$ to about 25 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

An oil-in-water emulsion is prepared by combining the following ingredients using conventional mixing techniques.

| Ingredients | Weight Percent |
| --- | --- |
| Phase A | |
| PPG-14 Butyl Ether | 8.00 |
| Salicylic Acid | 2.00 |
| Polyquaternium 37 (and) Mineral Oil (and) PPG-1 trideceth-6[1] | 1.50 |
| Polydimethylsiloxane Treated Fumed Silica[2] | 0.90 |
| Cetyl Alcohol | 0.75 |
| Stearyl Alcohol | 0.75 |
| Dimethicone[3] | 0.60 |
| Steareth-2 | 0.05 |
| Phase B | |
| Water | QS100 |
| Glycerol | 3.00 |
| Steareth-21 | 0.45 |
| Tetrasodium EDTA | 0.02 |
| Triethanolamine | 0.15 |
| Phase C | |
| Dimethicone (and) Cyclomethicone[4] | 0.50 |
| Fragrance | 0.20 |

[1]Available as Salcare SC95 from Allied Colloids, Norfolk, VA.
[2]Available as CAB-O-Sil® TS-720 from Cabot Corporation, Tuscola, IL.
[3]Available as Dow Corning 200/350 centistoke fluid.
[4]Available as Dow Corning Q2-1401 fluid which is a mixture of 10% dimethicone and 90% cyclomethicone.

In a suitable vessel, the phase A ingredients are combined and heated with mixing to 75°–80° C. until a liquid oil phase is formed. In a separate vessel, the phase B ingredients are heated with mixing to 75°–80° C. to form a water phase. Next, the oil phase is added to the water phase with mixing to form an emulsion. Next, the emulsion is cooled with mixing to 35° C. Next, the Phase C ingredients are added to the emulsion with mixing and then cooled to room temperature.

This emulsion is useful for topical application to the skin.

In an alternate embodiment, the polydimethylsiloxane treated fumed silica is replace with an equal weight of crosslinked polymethacrylate copolymer available as Polytrap® 6603 from Dow Corning Corp., Midland, Mich.

Example 2

An oil-in-water emulsion is prepared by combining the following ingredients using conventional mixing techniques.

| Ingredients | Weight Percent |
| --- | --- |
| Phase A | |
| Octyl Methoxycinnamate | 7.50 |
| Isohexadecane | 3.00 |
| Stearic Acid | 1.00 |
| Cetyl Alcohol | 1.06 |
| Crosslinked Polymethacrylate Copolymer[1] | 1.00 |
| DEA Cetyl Phosphate | 0.75 |
| Titanium Dioxide | 0.50 |
| Cetyl Palmitate | 0.50 |
| Propylparaben | 0.15 |
| PEG-10 Soya Sterol Oil | 0.10 |
| Castor Oil | 0.05 |
| Aluminum Starch Octenyl Succinate | 0.50 |
| Phase B | |
| Water | QS100 |
| Butylene Glycol | 2.00 |
| Glycerol | 1.00 |
| Methylparaben | 0.25 |
| Carbomer 954 | 0.20 |
| Acrylates/C10-30 Alkyl Acrylate Crosspolymer[2] | 0.13 |
| Disodium EDTA | 0.05 |
| Phase C | |
| Water | 2.00 |
| Triethanolamine | 1.30 |
| 2-Phenylbenzimidazole 5-Sulfonic Acid | 1.00 |
| Phase D | |
| Water | 2.00 |
| Imidazolidinyl Urea | 0.30 |
| Phase E | |
| Fragrance | 0.20 |

[1]Available as Polytrap® 6603 from Dow Corning Corp., Midland, MI.
[2]Available as Pemulen TR-1 from B.F. Goodrich Corp., Akron, OH.

In a suitable vessel, the phase A ingredients are combined and heated with mixing to 75° C. until a liquid oil phase is formed. In a separate vessel, the phase B ingredients are heated with mixing to 75° C. to form a water phase. Next, the oil phase is added to the water phase with mixing to form an emulsion. The emulsion is then mixed with cooling to 35° C. at which time the phase C, D and E ingredients are added with mixing. The emulsion is then cooled to room temperature.

This emulsion is useful for topical application to the skin to provide protection from the harmful effects of ultraviolet radiation.

In an alternate embodiment the crosslinked polymethacrylate copolymer is replaced with an equal weight of polydiemthylsiloxane treated fumed silica available as CAB-O-Sil® TS-720 from Cabot Corporation, Tuscola, Ill.

Example 3

An oil-in-water emulsion is prepared by combining the following ingredients using conventional mixing techniques.

| Ingredients | Weight Percent |
| --- | --- |
| Phase A | |
| Octyl Methoxycinnamate | 7.50 |
| PPG-14 Butyl Ether | 3.00 |
| Salicylic Acid | 2.00 |
| Tocopherol Acetate | 1.00 |
| Polydimethylsiloxine Treated Fumed Silica[1] | 0.90 |
| Polypropylene[2] | 0.50 |
| Steareth-21 | 0.45 |
| Phase B | |
| Water | QS100 |
| 2-Phenylbenzimidazole-5-Sulfonic Acid | 1.00 |
| Glycerol | 1.50 |
| Steareth-2 | 0.45 |
| Hydroxyethylcellulose | 0.20 |
| Triethanolamine | 0.10 |
| Tetrasodium EDTA | 0.02 |
| Phase C | |
| Polyquaternium 37 (and) Mineral Oil (and) PPG-1 trideceth-6[3] | 2.00 |
| Phase D | |
| Dimethicone (and) Dimethiconol[4] | 1.50 |
| Phase E | |
| Fragrance | 0.20 |

[1]Available as CAB-O-Sil® TS-720 from Cabot Corporation, Tuscola, IL.
[2]Available as Propylmatte from Micro Powders, Tarrytown, NY.
[3]Available as Salcare SC95 from Allied Colloids, Norfolk, VA.
[4]Available as Q21403 from Dow Corning which is a mixture of 85% dimethicone and 15% dimehticonol.

In a suitable vessel, the phase A ingredients are combined and heated with mixing to 75° C. until a liquid oil phase is formed. In a separate vessel, the phase B ingredients are heated with mixing to 75° C. to form a water phase. Next, the oil phase is added to the water phase with mixing to form an emulsion. Next, the phase C ingredient is added to the emulsion with mixing and then cooled to room temperature. Next, the phase D and E ingredients are added with mixing.

This emulsion is useful for topical application to the skin to provide protection from the harmful effects of ultraviolet radiation.

In an alternate procedure, the 2-phenylbenzimidazole-5-sulfonic acid is incorporated in with phase A.

What is claimed is:

1. An oil-in-water emulsion composition useful for topical application to human skin comprising:
   (a) from about 5% to about 60% by weight of the total composition of an oil phase having a viscosity from about 3000 cps, measured at 25° C. using a Brook fled RVT viscometer equipped with a T bar "B" spindle rotating at 5 rpm, to about 10,000,000 cps, measured at 25° C. using a Brookfied RVT viscometer equipped with a T bar "F" spindle rotating at 0.5 rpm, wherein said oil phase comprises
      (i) from about 0.1% to about 10% by weight of the total composition of a particulate thickener selected from the group consisting of chemically treated or coated silica, polymethacrylate polymers, polymethacrylate and styrene copolymers, treated calcium silicate, treated bentonite, treated hectorite, and mixtures thereof; and
      (ii) from 0% to about 10% by weight of the total composition of an oil phase emulsifier; and
   (b) from about 40% to about 95% by weight of the total composition of an aqueous phase selected from the group consisting of water, water-miscible solvents, and mixtures thereof, wherein said aqueous phase comprises
      (i) from 0% to about 10% by weight of the total composition of an aqueous phase emulsifier,
   wherein the percentage by weight of the oil phase emulsifier and of the aqueous phase emulsifier are not simultaneously zero.

2. An emulsion composition according to claim 1 wherein said particulate thickener is a chemically treated or coated silica.

3. An emulsion composition according to claim 2 wherein said chemically treated or coated silica is a chemically treated or coated fumed silica.

4. An emulsion composition according to claim 3 wherein said chemically treated or coated fumed silica has a mean agglomerate particle size from about 1 nm to about 50 nm and a moan aggregate particle size from about 0.01 nm to about 15 nm.

5. An emulsion composition according to claim 4 wherein said chemically treated or coated fumed silica is selected from the group consisting of polyalkylsiloxane treated fumed silica, trialkylsilanized fumed silica, dialkyldisilanized fumed silica, and mixtures thereof.

6. An emulsion composition according to claim 5 wherein said chemically treated or coated fumed silica is selected from the group consisting of polydiemthylsiloxane treated fumed silica, trimethylsilanized fumed silica, dialkyldisilanized fumed silica, and mixtures thereof.

7. An emulsion composition according to claim 6 wherein said chemically treated or coated fumed silica is a polydimethylsiloxane treated fumed silica having a surface area of about 80 to about 120 $m^2$/g and a bulk density of about 50 g/liter.

8. An emulsion composition according to claim 7 wherein said oil phase emulsifier is selected from the group consisting of steareth-2, PEG-5 soya sterol oil, PEG-10 Soya sterol oil, diethanolamine cetyl phosphate, sorbitan monostearate, diethylenglycol monostearate, glyceryl monostearate, and mixtures thereof, and wherein said aqueous phase emulsifier is selected from the group consisting of Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 methyl glucoside sesquistearate, PEG-20 glyceryl monostearate, sucrose monostearate, sucrose polystearates, polyglyceryl 10 stearate, polyglceryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, and mixtures thereof.

9. An emulsion composition according to claim 8 wherein said oil phase emulsifier is steareth-2 and wherein said aqueous phase emulsifier is steareth-21.

10. An emulsion composition according to claim 8 wherein said emulsion composition comprises an active ingredient selected from the group consisting of anti-acne actives, nonsteroidal antiinflammatory actives, anti-skin wrinkling actives, anti-pruritic actives, anesthetic actives, antimicrobial actives, sunscreening actives, sunless tanning actives, skin lightening actives, and mixtures thereof.

11. An emulsion composition according to claim 10 wherein said active ingredient is a sunscreen active selected from the group consisting of 2-ethylhexyl p-methoxycinnamate, 2-ethylhexyl N,N-dimethyl-p-aminobenzoate, p-aminobenzoic acid, octocrylene, oxybenzone, homomenthyl salicylate, 2-phenylbenzimidazole-5-sulfonic acid, octyl salicylate, 4,4'-methoxy-t-butyldibenzoylmethane, 4-isopropyl dibenzoyl methane, 3-benzylidene camphor, 3-(4-methylbenzylidene) camphor, triethanolamine salicylate, titanium dioxide, zinc oxide, iron oxide, 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N- (2-ethylhexyl)methylaminobenzoic acid ester of 2-hydroxy-4-(2-hydroxyethoxy-)benzophenone, 4-N,N-(2-ethylhexyl)-methylaminobenzoic acid ester of 4-(2-hydroxyethoxy)dibenzoylmethane, and mixtures thereof.

12. An emulsion composition according to claim 10 wherein said active ingredient is an anti-skin wrinkling active selected from the group consisting of salicylic acid, glycolic acid, lactic acid, retinoic acid, and mixtures thereof.

13. A emulsion composition according to claim 12 wherein said anti-skin wrinkling active is salicylic acid.

14. An emulsion composition according to claim 10 which further comprises from about 0.1% to about 20% of a humectant.

15. An emulsion composition according to claim 14 wherein said humectant is glycerol.

16. A method for treating human skin, said method comprising topically applying to the skin of a human an effective amount of an emulsion composition according to claim 10.

17. A method for providing enhanced protection to the skin of humans from the effects of ultraviolet radiation, said method comprising topically applying to the skin of a human an effective amount of an emulsion composition according to claim 11.

* * * * *

UNITED STATES PATENT AND TRADEMARK OFFICE
CERTIFICATE OF CORRECTION

PATENT NO.    :   5,618,522

DATED         :   April 8, 1997

INVENTOR(S)   :   James E. Kaleta et al.

It is certified that error appears in the above-identified patent and that said Letters Patent is hereby corrected as shown below:

At column 1, line 15 "known is since" should read --known since--.

At column 2, line 8 "Brookfied" should read --Brookfield--.

At column 2, line 10 "Brookfied" should read --Brookfield--.

At column 2, line 60 "Brookfied" should read --Brookfield--.

At column 2, line 63 "Brookfied" should read --Brookfield--.

At column 3, line 65 "Brookfied" should read --Brookfield--.

At column 3, line 67 "Brookfied" should read --Brookfield--.

At column 4, line 54 "weighted is arithmetic" should read --weighted arithmetic--.

At column 6, line 11 "ller" should read --Iler--.

At column 12, line 64 "$C_{1-4}$ alkyl —CN —COOH and" should read --$C_{1-4}$ alkyl, —CN,— —COOH, and--.

At column 13, line 2 "(i e." should read --(i.e.,--.

At column 13, line 9 "acryl" should read --acrylic--.

At column 13, line 12 "$C_{1-4}$ alkyl —CN" should read --$C_{1-4}$ alkyl, —CN--.

At column 13, line 25 "esters $C_{1-4}$" should read --esters, $C_{1-4}$--.

At column 13, line 27 "esters $C_{1-4}$" should read --esters, $C_{1-4}$--.

At column 14, line 23 "I or m" should read --l or m--.

At column 14, line 35 "short is chain" should read --short chain--.

At column 14, line 36 "alkyls i.e. $C_1$-$C_8$" should read --alkyls, i.e., $C_1$-$C_8$--.

At column 15, line 64 "I is zero" should read --l is zero--.

At column 16, line 3 "PPG-1l" should read --PPG-1--.

At column 18, line 20 "dimethylacrylamide" should read --N,N-dimethylacrylamide--.

At column 20, line 23 "1.06" should read --1.00--.

UNITED STATES PATENT AND TRADEMARK OFFICE
CERTIFICATE OF CORRECTION

PATENT NO.    :    5,618,522

DATED         :    April 8, 1997

INVENTOR(S)   :    James E. Kaleta et al.

It is certified that error appears in the above-identified patent and that said Letters Patent is hereby corrected as shown below:

At column 21, line 13 "Polydimethylsiloxine" should read --Polydimethylsiloxane--.

At column 21, line 25 "Polyquatemium 37" should read --Polyquaternium 37--.

At column 21, line 55 "Brook fled" should read --Brookfield--.

At column 21, line 58 "Brookfied" should read --Brookfield--.

At column 22, line 22 "moan" should read --mean--.

At column 22, line 31 "polydiemthylsiloxane" should read --polydimethylsiloxane--.

At column 23, line 8 "dibenzoyl methane" should read --dibenzoylmethane--.

Signed and Sealed this

Seventh Day of October, 1997

Attest:

BRUCE LEHMAN

Attesting Officer

Commissioner of Patents and Trademarks